(12) United States Patent
Moffitt et al.

(10) Patent No.: US 10,744,330 B2
(45) Date of Patent: *Aug. 18, 2020

(54) USER INTERFACE FOR SEGMENTED NEUROSTIMULATION LEADS

(71) Applicant: Boston Scientific Neuromodulation Corporation, Valencia, CA (US)

(72) Inventors: Michael A. Moffitt, Saugus, CA (US); Sridhar Kothandaraman, Valencia, CA (US); James Carl Makous, N. Potomac, MD (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 15/900,644

(22) Filed: Feb. 20, 2018

(65) Prior Publication Data

US 2018/0178021 A1  Jun. 28, 2018

Related U.S. Application Data

(60) Continuation of application No. 15/208,413, filed on Jul. 12, 2016, now Pat. No. 9,931,512, which is a (Continued)

(51) Int. Cl.
*A61N 1/36* (2006.01)
*A61N 1/372* (2006.01)
(Continued)

(52) U.S. Cl.
CPC ....... *A61N 1/37247* (2013.01); *A61N 1/0534* (2013.01); *A61N 1/36064* (2013.01);
(Continued)

(58) Field of Classification Search
CPC ............ A61N 1/37247; A61N 1/36185; A61N 1/0534; A61N 1/36082; A61N 1/36064;
(Continued)

(56) References Cited

U.S. PATENT DOCUMENTS 6,516,227 B1  2/2003  Meadows et al.
6,609,032 B1 *  8/2003  Woods ............... A61N 1/36071
607/46
(Continued)

FOREIGN PATENT DOCUMENTS

| WO | 2009134475 | 11/2009 |
| WO | 2010065888 | 6/2010 |
| WO | 2012024441 | 2/2012 |

OTHER PUBLICATIONS

"U.S. Appl. No. 13/212,063, Advisory Action dated Sep. 2, 2015", 2 pgs.
(Continued)

*Primary Examiner* — Amanda K Hulbert
*Assistant Examiner* — Natasha Patel
(74) *Attorney, Agent, or Firm* — Lowe Graham Jones PLLC; Bruce E. Black

(57) ABSTRACT

An external control device for use with a neurostimulation system having a plurality of electrodes capable of conveying an electrical stimulation field into tissue in which the electrodes are implanted is provided. The external control device comprises a user interface having one or more control elements, a processor configured for generating stimulation parameters designed to modify the electrical stimulation field relative to one or more neurostimulation lead carrying the electrodes. The external control device further comprises output circuitry configured for transmitting the stimulation parameters to the neurostimulation system.

20 Claims, 11 Drawing Sheets

Related U.S. Application Data division of application No. 13/212,063, filed on Aug. 17, 2011, now Pat. No. 9,411,935.

(60) Provisional application No. 61/374,879, filed on Aug. 18, 2010.

(51) Int. Cl.
*A61N 1/05* (2006.01)
*G16H 40/63* (2018.01)

(52) U.S. Cl.
CPC ..... *A61N 1/36067* (2013.01); *A61N 1/36071* (2013.01); *A61N 1/36082* (2013.01); *A61N 1/36185* (2013.01); *G16H 40/63* (2018.01); *A61N 1/36182* (2013.01)

(58) Field of Classification Search
CPC ............ A61N 1/36067; A61N 1/36071; A61N 1/36182; G16H 40/63
See application file for complete search history.

(56) References Cited

U.S. PATENT DOCUMENTS

| | | | |
|---|---|---|---|
| 6,845,267 B2 | 1/2005 | Harrison et al. | |
| 6,895,280 B2 | 5/2005 | Meadows et al. | |
| 6,950,707 B2 | 9/2005 | Whitehurst | |
| 6,993,384 B2 | 1/2006 | Bradley et al. | |
| 7,346,382 B2 | 3/2008 | McIntyre et al. | |
| 7,650,184 B2 | 1/2010 | Walter | |
| 2003/0176899 A1 | 9/2003 | Samuelsson et al. | |
| 2006/0017749 A1 | 1/2006 | Mcintyre et al. | |
| 2006/0235332 A1* | 10/2006 | Smoorenburg | A61N 1/37247 600/559 |
| 2007/0055322 A1 | 3/2007 | Forsberg et al. | |
| 2007/0168004 A1 | 7/2007 | Walter | |
| 2007/0168007 A1 | 7/2007 | Kuzma et al. | |
| 2007/0203537 A1* | 8/2007 | Goetz | A61N 1/0529 607/59 |
| 2007/0203538 A1 | 8/2007 | Stone et al. | |
| 2007/0203539 A1 | 8/2007 | Stone et al. | |
| 2007/0203542 A1 | 8/2007 | Goetz et al. | |
| 2007/0203545 A1 | 8/2007 | Stone et al. | |
| 2007/0203546 A1 | 8/2007 | Stone et al. | |
| 2008/0109048 A1 | 5/2008 | Moffitt | |
| 2008/0154340 A1 | 6/2008 | Goetz et al. | |
| 2008/0215125 A1 | 9/2008 | Farah et al. | |
| 2009/0018617 A1 | 1/2009 | Skelton et al. | |
| 2009/0118787 A1 | 5/2009 | Moffitt et al. | |
| 2009/0287271 A1* | 11/2009 | Blum | A61N 1/37247 607/45 |
| 2009/0287272 A1 | 11/2009 | Kokones et al. | |
| 2009/0287273 A1 | 11/2009 | Carlton et al. | |
| 2009/0287467 A1 | 11/2009 | Sparks et al. | |
| 2009/0326608 A1 | 12/2009 | Huynh et al. | |
| 2010/0001566 A1 | 1/2010 | Yehuda | |
| 2010/0010566 A1 | 1/2010 | Thacker et al. | |
| 2010/0010623 A1 | 1/2010 | Lashinski et al. | |
| 2010/0023090 A1 | 1/2010 | Jaax et al. | |
| 2010/0049276 A1 | 2/2010 | Blum et al. | |
| 2010/0106231 A1 | 4/2010 | Torgerson et al. | |
| 2010/0121409 A1 | 5/2010 | Kothandaraman et al. | |
| 2011/0270357 A1 | 11/2011 | Torgerson et al. | |
| 2012/0046715 A1 | 2/2012 | Moffitt et al. | |
| 2013/0226261 A1 | 8/2013 | Sparks et al. | |

OTHER PUBLICATIONS

"U.S. Appl. No. 13/212,063, Advisory Action dated Nov. 13, 2013", 3 pgs.
"U.S. Appl. No. 13/212,063, Examiner Interview Summary dated Feb. 11, 2016", 3 pgs.
"U.S. Appl. No. 13/212,063, Final Office Action dated Jun. 17, 2015", 7 pgs.
"U.S. Appl. No. 13/212,063, Final Office Action dated Sep. 16, 2014", 6 pgs.
"U.S. Appl. No. 13/212,063, Non Final Office Action dated Jan. 26, 2015", 7 pgs.
"U.S. Appl. No. 13/212,063, Non Final Office Action dated Apr. 2, 2014", 7 pgs.
"U.S. Appl. No. 13/212,063, Non Final Office Action dated Nov. 13, 2015", 7 pgs.
"U.S. Appl. No. 13/212,063, Response filed Feb. 4, 2014 to Restriction Requirement dated Jan. 10, 2014", 6 pgs.
"U.S. Appl. No. 13/212,063, Response filed Apr. 27, 2015 to Non Final Office Action dated Jan. 26, 2015", 9 pgs.
"U.S. Appl. No. 13/212,063, Response filed Jul. 11, 2014 to Non Final Office Action dated Apr. 2, 2014", 6 pgs.
"U.S. Appl. No. 13/212,063, Response filed Aug. 17, 2015 to Final Office Action dated Jun. 17, 2015", 9 pgs.
"U.S. Appl. No. 13/212,063, Response filed Oct. 15, 2015 to Advisory Action dated Sep. 2, 2015", 14 pgs.
"U.S. Appl. No. 13/212,063, Response filed Nov. 3, 2014 to Final Office Action dated Sep. 16, 2014", 8 pgs.
"U.S. Appl. No. 13/212,063, Response filed Dec. 15, 2014 to Advisory Action dated Nov. 13, 2014", 7 pgs.
"U.S. Appl. No. 13/212,063, Response filed 13/212,063, to Non Final Office Action dated Nov. 13, 2015", 10 pgs.
"U.S. Appl. No. 13/212,063, Restriction Requirement dated Jan. 10, 2014", 7 pgs.
"Australian Application Serial No. 2011292025, First Examiner Report dated Nov. 6, 2015", 5 pgs.
"European Application Serial No. 11750031.4, Office Action dated Apr. 11, 2013", 2 pgs.
"European Application Serial No. 11750031.4, Response filed Oct. 16, 2013 to Office Action dated Apr. 11, 2013", 7 pgs.
"European Application Serial No. 13156700.0, Extended European Search Report dated Jul. 24, 2013", 8 pgs.
"European Application Serial No. 13156700.0, Response filed Feb. 28, 2014 to Extended European Search Report dated Jul. 24, 2013", 10 pgs.
"International Application Serial No. PCT/US2011/048144, International Preliminary Report on Patentability dated Feb. 28, 2013", 12 pgs.
"International Application Serial No. PCT/US2011/048144, International Search Report dated Mar. 9, 2012", 7 pgs.
"International Application Serial No. PCT/US2011/048144, Written Opinion dated Mar. 9, 2012", 10 pgs.
"Japanese Application Serial No. 2013-524969, Office Action dated Apr. 13, 2015", English Translation, 9 pgs.
"Japanese Application Serial No. 2013-524969, Office Action dated Nov. 11, 2015", 5 pgs.
"Japanese Application Serial No. 2013-524969, Office Action dated May 23, 2016", 4 pgs.
Frankemolle, Anneke, et al., "Reversing cognitive-motor impairments in Parkinson's disease patients using a computational modelling approach to deep brain stimulation programming", Brain, 133, (2010), 746-761.
Hunka, Karen, et al., "Nursing Time to Program and Assess Deep Brain Stimulators in Movement Disorder Patients", Journal of Neuroscience Nursing, vol. 37, (Aug. 2005), 204-210.
"U.S. Appl. No. 13/212,063, Notice of Allowance dated Apr. 5, 2016", 5 pgs.
Official Communication for U.S. Appl. No. 15/208,413 dated Sep. 9, 2016.
Official Communication for U.S. Appl. No. 15/208,413 dated Mar. 22, 2017.
Official Communication for U.S. Appl. No. 15/208,413 dated Sep. 28, 2017.

* cited by examiner

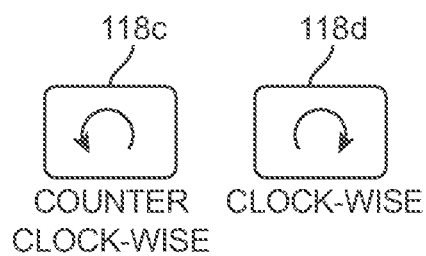
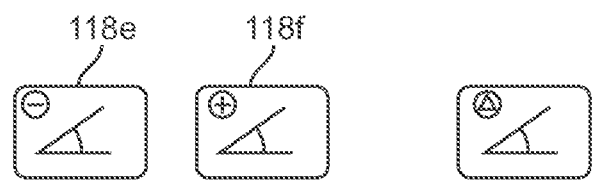
FIG. 11A  FIG. 11B  FIG. 11C
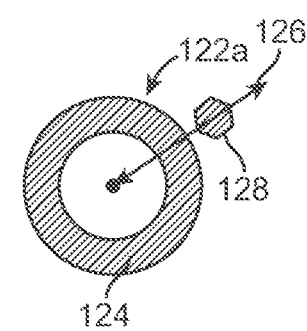
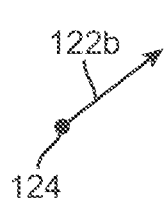
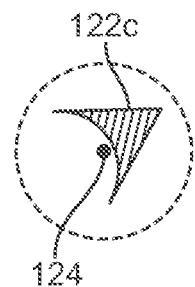
FIG. 12A  FIG. 12B  FIG. 12C
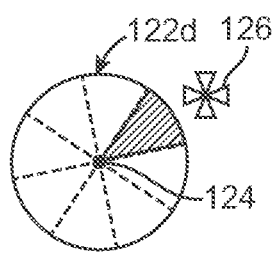
FIG. 12D
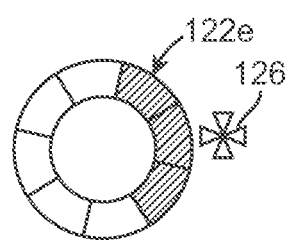
FIG. 12E
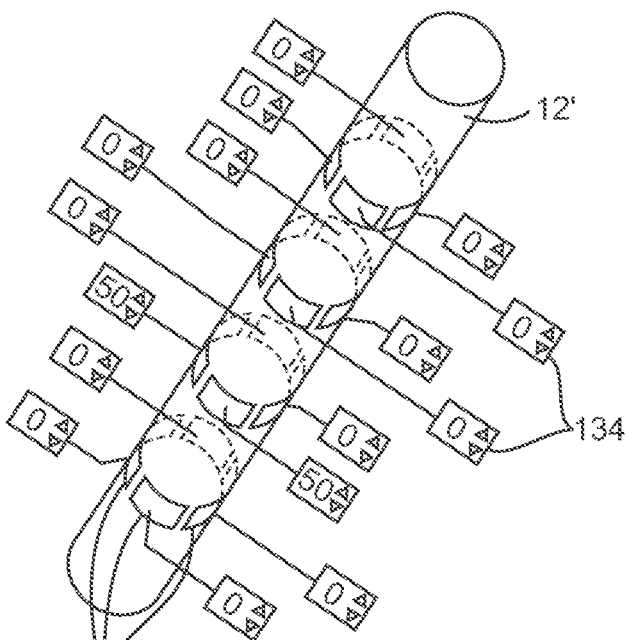
FIG. 13

USER INTERFACE FOR SEGMENTED NEUROSTIMULATION LEADS

RELATED APPLICATION DATA

The present application is a continuation of U.S. patent application Ser. No. 15/208,413 filed Jul. 12, 2016, which is a divisional of U.S. application Ser. No. 13/212,063 filed Aug. 17, 2011, which issued as U.S. Pat. No. 9,411,935, and which claims the benefit under 35 U.S.C. § 119 to U.S. provisional patent application Ser. No. 61/374,879, filed Aug. 18, 2010. The foregoing applications are hereby incorporated by reference into the present application in their entirety.

FIELD OF THE INVENTION

The present invention relates to tissue stimulation systems, and more particularly, to user interfaces and methods for controlling the distribution of electrical current on segmented neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation. More pertinent to the present inventions described herein, Deep Brain Stimulation (DBS) has been applied therapeutically for well over a decade for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707, which are expressly incorporated herein by reference.

Each of these implantable neurostimulation systems typically includes one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of movement disorders), while minimizing the volume of non-target tissue that is stimulated. A typical stimulation parameter set may include the electrodes that are acting as anodes or cathodes, as well as the amplitude, duration, and rate of the stimulation pulses.

Significantly, non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects.

For example, bilateral DBS of the subthalamic nucleus has been proven to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16). In large part, this phenomenon is due to the small size of the subthalamic nucleus. Even with the electrodes are located predominately within the sensorimotor territory, the electrical field generated by DBS is non-discriminately applied to all neural elements surrounding the electrodes, thereby resulting in the spread of current to neural elements affecting cognition. As a result, diminished cognitive function during stimulation of the subthalamic nucleus may occur do to non-selective activation of non-motor pathways within or around the subthalamic nucleus.

The large number of electrodes available, combined with the ability to generate a variety of complex stimulation pulses, presents a huge selection of stimulation parameter sets to the clinician or patient. In the context of DBS, neurostimulation leads with a complex arrangement of electrodes that not only are distributed axially along the leads, but are also distributed circumferentially around the neurostimulation leads as segmented electrodes, can be used.

To facilitate such selection, the clinician generally programs the external control device, and if applicable the neurostimulator, through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

As physicians and clinicians become more comfortable with implanting neurostimulation systems and time in the operating room decreases, post-implant programming sessions are becoming a larger portion of process. Furthermore, because the body tends to adapt to the specific stimulation parameters currently programmed into a neurostimulation system, or the full effects of stimulation are not manifest in a short period of time (i.e., not observed within a programming session), follow-up programming procedures are often needed. For example, the brain is dynamic (e.g., due to disease progression, motor re-learning, or other changes), and a program (i.e., a set of stimulation parameters) that is useful for a period of time may not maintain its effectiveness and/or the expectations of the patient may increase. Further, physicians typically treat the patient with stimulation and medication, and proper amounts of each are required for optimal therapy. Thus, after the DBS system has been implanted and fitted, the patient may have to schedule another visit to the physician in order to adjust the stimulation parameters of the DBS system if the treatment provided by the implanted DBS system is no longer effective or otherwise is not therapeutically or operationally optimum due to, e.g., disease progression, motor re-learning, or other changes. Clinical estimates suggest that 18-36 hours per patient are necessary to program and assess DBS patients with current techniques (see Hunka K., et al., *Nursing Time to Program and Assess Deep Brain Stimulators in Movement Disorder Patients,* J. Neursci Nurs. 37: 204-10).

There, thus, remains a need for a user interface that more efficiently allows the programming of neurostimulation systems that utilize neurostimulation leads with complex electrode arrangements.

SUMMARY OF THE INVENTION

The present inventions are directed to external control device (e.g., a clinician's programmer) for use with a neurostimulation system having a plurality of electrodes (which may be carried by one or more neurostimulation leads) capable of conveying an electrical stimulation field into tissue in which the electrodes are implanted is provided. The external control device comprises a user interface having one or more control elements, a processor configured for generating stimulation parameters designed to modify the electrical stimulation field relative to the neurostimulation lead(s). In the case of a single neurostimulation lead, the set stimulation parameter set is designed to modify the electrical stimulation field relative to the axis of the single neurostimulation lead. The external control device further comprises output circuitry (e.g., telemetry circuitry) configured for transmitting the stimulation parameters to the neurostimulation system. The user interface may further include a display screen, in which case, the control element(s) may take the form of icons on the display screen. The external control device may further comprise a housing containing the user interface, processor, and output circuitry.

In accordance with one aspect of the present inventions, the user interface includes a mode selection control element and an electrical stimulation field modification control element, and the processor is configured for selectively placing the electrical stimulation field modification control element between an electrical stimulation field displacement mode and an electrical stimulation field shaping mode when the mode selection control element is actuated. The processor is further configured for generating a first set of stimulation parameters designed to displace a locus of the electrical stimulation field when the electrical stimulation field modification control element is actuated in the electrical stimulation field displacement mode, and for generating a second set of stimulation parameters designed to shape the electrical stimulation field about its locus when the electrical stimulation field modification control element is actuated in the electrical stimulation field shaping mode.

In one embodiment, the electrodes are arranged axially along one or more neurostimulation leads, in which case, the first set of stimulation parameters may be designed to displace the electrical stimulation field along the neurostimulation lead(s), and the second set of stimulation parameters may be designed to expand or contract the electrical stimulation field along the neurostimulation lead(s). In another embodiment, the electrodes are arranged circumferentially about the one or more neurostimulation leads, in which case, the first set of stimulation parameters may be designed to displace the electrical stimulation field about the neurostimulation lead(s), and the second set of stimulation parameters may be designed to expand or contract the electrical stimulation field about the neurostimulation lead(s).

In accordance with a second aspect of the present inventions, the user interface includes a circumferential modification control element configured for being actuated (e.g., a rotational control element configured for being rotated about a point), and the processor is configured for generating a set of stimulation parameters designed to circumferentially displace a locus of the electrical stimulation field about the neurostimulation lead(s) when the rotational control element is rotated about the point.

In an optional embodiment, the user interface includes a marker associated with the rotational control element. The marker indicates the circumferential position of the locus of the electrical stimulation field. In another optional embodiment, the user interface includes a radial modification control element, and the processor is further configured for generating another set of stimulation parameters designed to radially displace the locus of the electrical stimulation field when the radial modification control element is actuated. The radial modification control element may be located on the rotational control element, in which case the radial modification control element may be configured for being radially displaced toward and away from the point of the rotational control element.

In accordance with a third aspect of the present invention, the user interface includes a circumferential modification control element configured for being continually (e.g., continuously or repeatedly) actuated, and the processor is configured for generating sets of stimulation parameters designed to circumferentially displace a locus of the electrical stimulation field about the neurostimulation lead(s) in a first rotational direction at respective different angular positions as the circumferential modification control element is continually actuated. The user interface may further include another circumferential modification control element configured for being continually actuated, in which case, the processor may be configured for generating other sets of stimulation parameters designed to circumferentially displace the locus of the electrical stimulation field about the neurostimulation lead(s) in a second rotational direction opposite to the first rotational direction at respective different angular positions as the other circumferential modification control element is continually actuated. In an optional embodiment, the user interface includes a radial modification control element, the processor is configured for generating another set of stimulation parameters designed to radially expand or contract the electrical stimulation field when the radial modification control element is actuated, and the output circuitry is configured for transmitting the other set of stimulation parameters to the neurostimulation system.

In accordance with a fourth aspect of the present inventions, the user interface includes a display screen (e.g., a touch screen) configured for displaying three-dimensional graphical renderings and a plurality of iconic control elements graphically linked to the three-dimensional renderings of the electrodes. The processor is configured for generating stimulation parameters designed to modify the electrical stimulation field when one of the iconic control elements is actuated. In one embodiment, the stimulation parameters define an amplitude of electrical current flowing through the electrode corresponding to the graphical rendering of the electrode to which the actuated iconic control element is graphically linked.

In another embodiment, the processor is configured for estimating a volume of tissue activation based on the generated stimulation parameters, and the display screen is configured for displaying an anatomical structure and the volume of tissue activation separately from the three-dimensional graphical renderings of the electrodes. In this case, the user interface includes a lead displacement control element configured for being actuated, and the processor is configured for synchronously displacing (e.g., axially and/or circumferentially) both the three-dimensional graphical rendering of the electrodes and the volume of tissue activation relative to the anatomical structure in response to the actuation of the lead displacement control element. The display screen may also be configured for displaying a three-dimensional graphical rendering of the neurostimulation lead with the volume of tissue activation and anatomical structure, and the processor is configured for synchronously displacing the three-dimensional graphical rendering of the electrodes and the volume of tissue activation and graphical rendering of the neurostimulation lead relative to the anatomical structure in response to the actuation of the lead displacement control element. The anatomical structure may be displayed in one of an axial view, a coronal view, and a sagittal view. In this case, the user interface may further include another control element configured for being actuated, and the processor may be configured for selecting one of the axial view, coronal view, and sagittal view in response to the actuation of the other control element.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 11A-11C are plan views illustrating alternative circumferential modification control elements that can be used in the user interface of FIG. 10;

FIGS. 12A-12E are plan views illustrating rotational control elements that can be used in the user interface of FIG. 10;

FIG. 13 is a perspective view of an alternative three-dimensional rendering of electrodes and control elements graphically associated with the electrode renderings that can be used with the user interface of FIG. 10;

DETAILED DESCRIPTION OF THE EMBODIMENTS

At the outset, it is noted that the present invention may be used with an implantable pulse generator (IPG), radio frequency (RF) transmitter, or similar neurostimulator, that may be used as a component of numerous different types of stimulation systems. The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder sublaxation, headache, etc.

Figure 1:
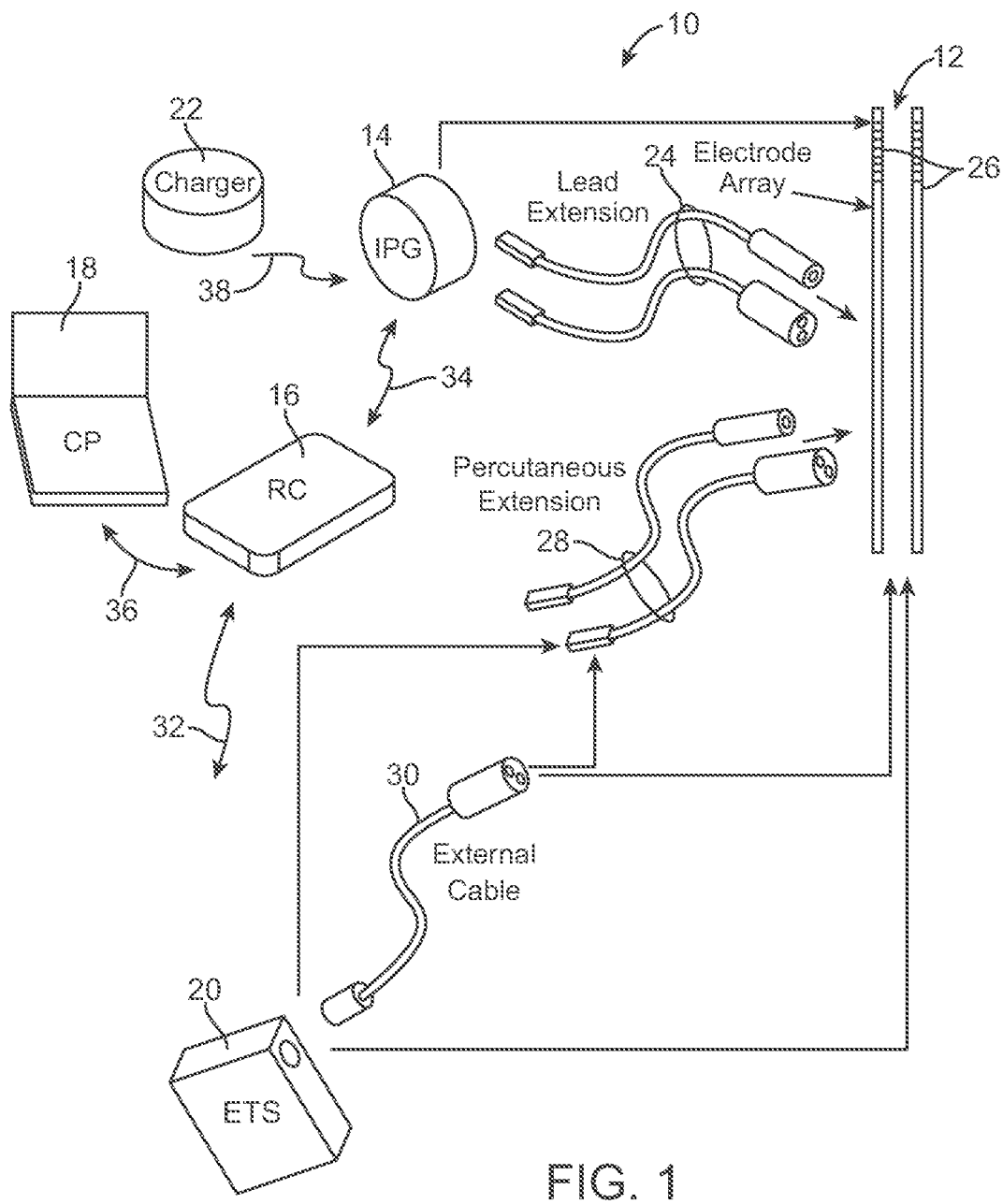
FIG. 1 is a plan view of a Deep Brain Stimulation (DBS) system constructed in accordance with one embodiment of the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, an external remote controller RC 16, a clinician's programmer (CP) 18, an External Trial Stimulator (electrodes ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
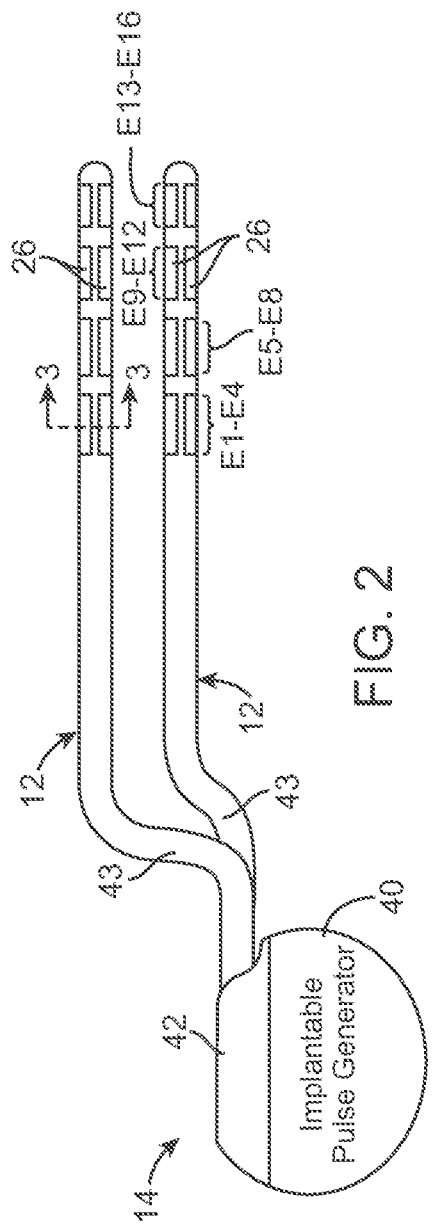
FIG. 2 is a profile view of an implantable pulse generator (IPG) and neurostimulation leads used in the DBS system of FIG. 1.

Referring to FIG. 2, the IPG 14 comprises an outer case 40 for housing the electronic and other components (described in further detail below), and a connector 42 to which the proximal end of the neurostimulation lead 12 mates in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Figure 3:
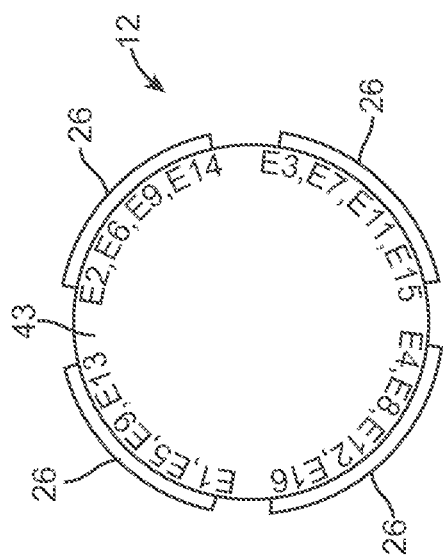
FIG. 3 is a cross-sectional view of a neurostimulation lead used in the DBS system of FIG. 1.

Each of the neurostimulation leads 12 comprises an elongated cylindrical lead body 43, and the electrodes 26 take the form of segmented electrodes that are circumferentially and axially disposed about the lead body 43. By way of non-limiting example, and with further reference to FIG. 3, each neurostimulation lead 12 may carry sixteen electrodes, arranged as four rings of electrodes (the first ring consisting of electrodes E1-E4; the second ring consisting of electrodes E5-E8; the third ring consisting of electrodes E9-E12; and the fourth ring consisting of E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Tripolar stimulation occurs when three of the lead electrodes 26 are activated, two as anodes and the remaining one as a cathode, or two as cathodes and the remaining one as an anode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

Figure 4:
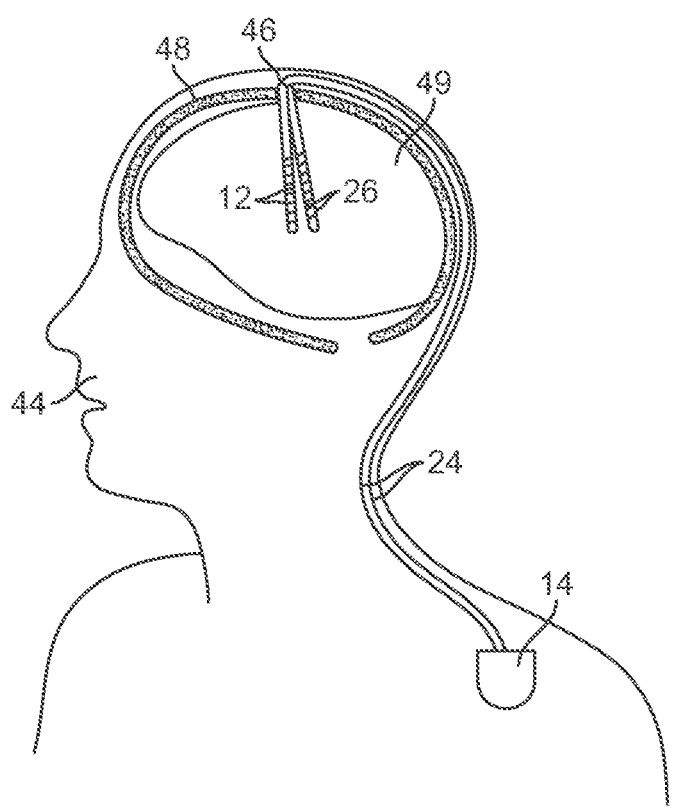
FIG. 4 is a cross-sectional view of a patient's head showing the implantation of stimulation leads and an IPG of the DBS system of FIG. 1.

As shown in FIG. 4, two percutaneous neurostimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

Figure 5:
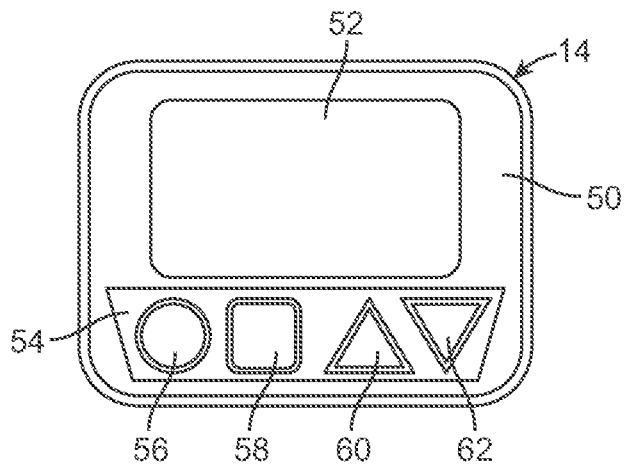
FIG. 5 is front view of a remote control (RC) used in the DBS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
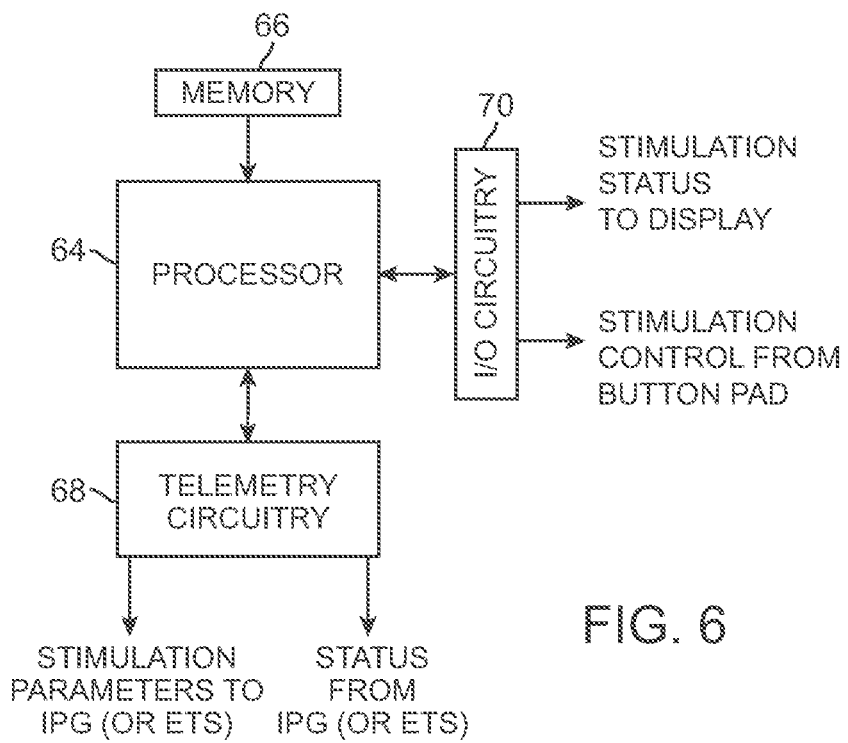
FIG. 6 is a block diagram of the internal components of the RC of FIG. 5.

Referring to FIG. 6, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 5). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 (or ETS 20) via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient response and feedback and for subsequently programming the IPG 14 (or ETS 20) with the optimum stimulation parameters.

Figure 7:
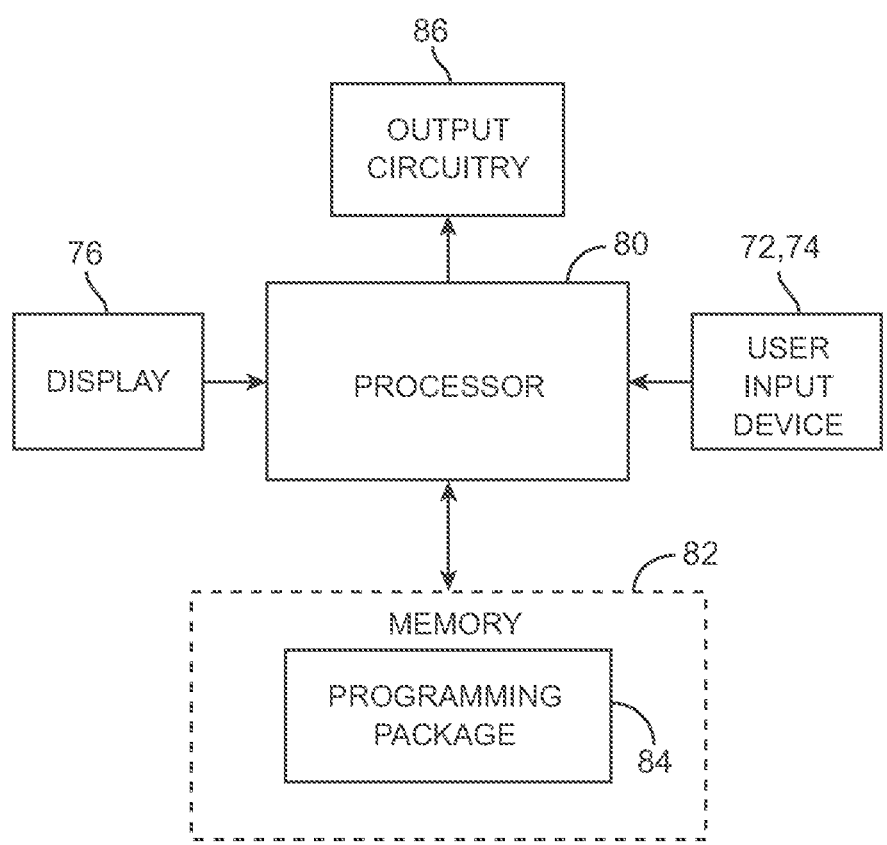
FIG. 7 is a block diagram of the internal components of a clinician's programmer (CP) used in the DBS system of FIG. 1.

To allow the user to perform these functions, the CP 18 includes a mouse 72, a keyboard 74, and a display screen 76 housed in a case 78. In the illustrated embodiment, display screen 76 is a conventional screen. It is to be understood that in addition to, or in lieu of, the mouse 72, other directional programming devices may be used, such as a trackball, touchpad, or joystick, can be used. Alternatively, instead of being conventional, the display screen 76 may be a digitizer screen, such as touchscreen) (not shown), may be used in conjunction with an active or passive digitizer stylus/finger touch. As shown in FIG. 7, the CP 18 generally includes a processor 80 (e.g., a central processor unit (CPU)) and memory 82 that stores a stimulation programming package 84, which can be executed by the processor 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 84 by the processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a more intuitive user interface that allows the electrical stimulation field conveyed by selected ones of the electrodes 26 to be modified, e.g., by axially, circumferentially, and/or radially displacing the locus of the stimulation field circumferentially relative to a single neurostimulation lead 12 or both neurostimulation leads 12, and axially and/or circumferentially expanding or contracting the electrical stimulation field about its locus.

Before discussing the intuitive user interface in detail, it will be useful to describe the various methods that can be used to modify the electrical stimulation field conveyed by the electrodes 26. For purposes of simplicity, the electrodes 26 will be described as being operated in a monopolar fashion, with one or more of the electrodes 26 arranged as a stimulating cathode ("−" polarity) and the case 40 arranged as the anode ("+" polarity), although the same principles described herein can be applied to the electrodes 26 when operated in a bipolar fashion.

In one method, different electrode combinations can be discretely selected to displace the locus of the electrical stimulation field from one location to another location within the electrode array 12.

Figure 8A:
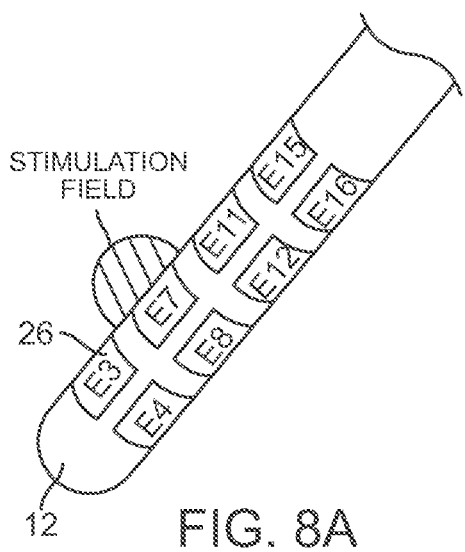
FIGS. 8A-8G are views showing activation of the electrodes to axially, circumferentially, and radially displace the locus of the electrical stimulation field relative to the neurostimulation lead.
Figure 8B:
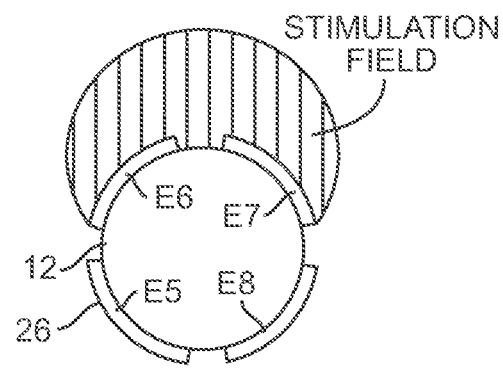

For example, with reference to FIGS. 8A and 8B, a first stimulating group of electrodes 26 consisting of two electrodes in the second ring and respectively in the second and third columns (electrodes E6, E7) can be activated as cathodes. This polarity and grouping causes electrical current to flow from the case electrode to electrodes E6 and E7 in a monopolar fashion, which results in a locus of the electrical stimulation field positioned equally between these two electrodes.

Figure 8C:
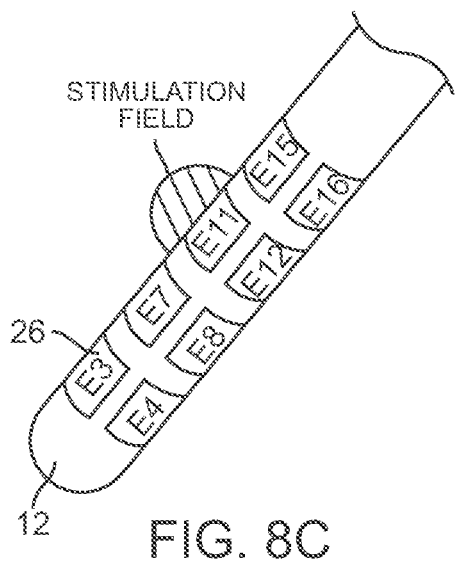

As shown in FIG. 8C, a second stimulating group of electrodes 26 consisting of two electrodes in the third ring (electrodes E10, E11) can be activated as cathodes. This polarity and grouping causes electrical current to flow from the case electrode to electrodes E10 and E11 in a monopolar fashion, which results in a locus of the electrical stimulation field positioned equally between these two electrodes. Thus, it can be appreciated from this that the locus of the electrical stimulation field can be axially displaced in the distal direction along the lead 12 by switching from the first stimulating group of electrodes (electrodes E6, E7) to the second stimulating group of electrodes (electrodes E10, E11), and can be axially displaced in the proximal direction along the lead 12 by switching from the second stimulating group of electrodes (electrodes E10, E11) to the first stimulating group of electrodes (electrodes E6, E7).

Figure 8D:
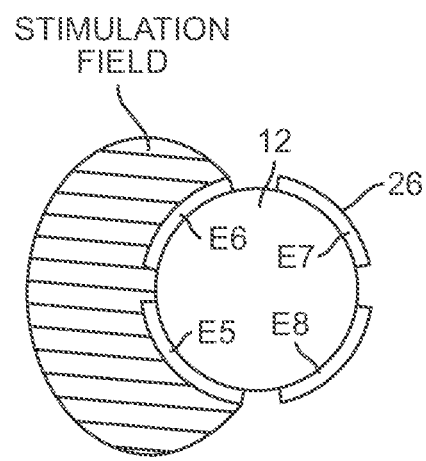

As shown in FIG. 8D, a third stimulating group of electrodes 26 consisting of an electrode in the first column (electrode E5) and an electrode in the second column (electrode E6) can be activated as cathodes. This polarity and grouping causes electrical current to flow from the case electrode to electrodes E5 and E6 in a monopolar fashion, which results in a locus of the electrical stimulation field positioned equally between these two electrodes. Thus, it can be appreciated from this that the locus of the electrical stimulation field can be circumferentially displaced in the counterclockwise direction about the lead 12 by switching from the first stimulating group of electrodes (electrodes E6, E7) to the fourth stimulating group of electrodes (electrodes E5, E6), and can be circumferentially displaced in the clockwise direction about the lead 12 by switching from the third stimulating group of electrodes (electrodes E6, E7) to the first stimulating group of electrodes (electrodes E5, E6).

Figure 8E:
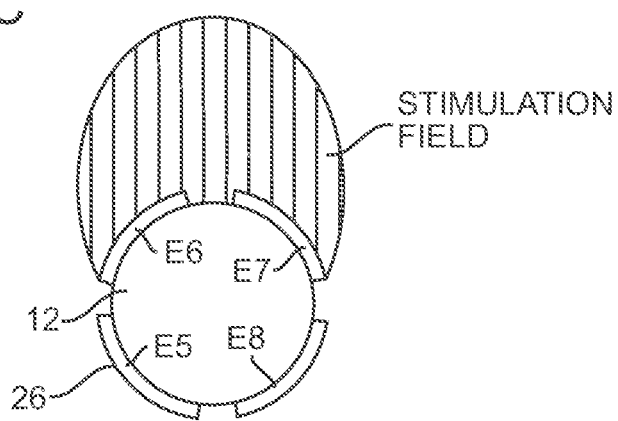

As shown in FIG. 8E, one or more electrodes 26 opposite the first stimulating group of electrodes 26, and in this case, electrodes E5 and E8, can be activated as an anode, and the amplitude of the current flowing through the first stimulating group of electrodes (electrodes E6, E7) can be increased to displace the locus of the electrical stimulation field radially outward from the lead 12. Electrodes E5 and E8, can be inactivated, and the amplitude of the current flowing through the first stimulating group of electrodes (electrodes E6, E7) can be decreased to displace the locus of the electrical stimulation field radially inward towards the lead 12.

Of course, other electrode combinations, including bipolar and tripolar combinations, can be selected to electronically displace the locus of the electrical stimulation field.

In another method, rather than discretely selecting different combinations of electrodes, electrical current can be gradually "steered" or shifted between electrodes to displace the locus of the electrical stimulation field.

Figure 8F:
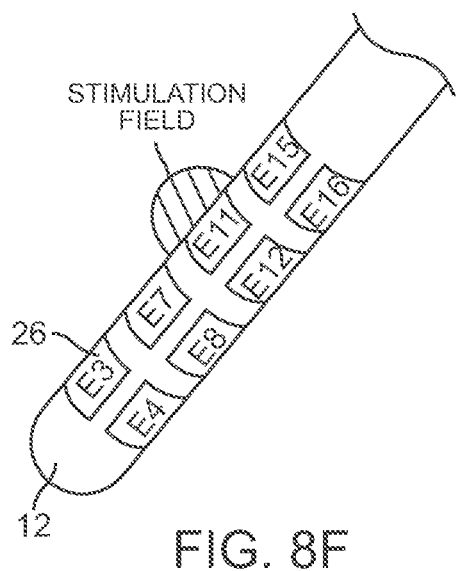

For example, assuming that electrodes E6 and E7 are the only electrodes in the stimulating group, the locus of the electrical stimulation field can be gradually displaced axially in the distal direction along the lead 12 by gradually including electrodes E10 and E11 in the stimulating electrode group and gradually excluding electrodes E6 and E7 from the stimulating electrode group. That is, the fractionalized cathodic current flowing through each of electrodes E10 and E11 is incrementally increased from 0% to 50%, while the fractionalized cathodic current flowing through each of electrodes E6 and E7 is incrementally decreased from 50% to 0%. As a result, the electrical stimulation field gradually moves from its initial position, as shown in FIG. 8A, to an axially displaced position, as shown in FIG. 8C. One incremental step may be, e.g., where fractionalized cathodic current flowing through each of electrodes E10 and E11 is 15%, and the fractionalized cathodic current flowing through each of electrodes E6 and E7 is 35%, in which case the electrical stimulation field may be in an axially displaced position, as shown in FIG. 8F.

Assuming that electrodes E10 and E11 are now the only electrodes in the stimulating group, the locus of the electrical stimulation field can be gradually displaced axially in the proximal direction along the lead 12 by gradually including electrodes E6 and E7 in the stimulating electrode group and gradually excluding electrodes E10 and E11 from the stimulating electrode group. That is, the fractionalized cathodic current flowing through each of electrodes E6 and E7 is incrementally increased from 0% to 50%, while the fractionalized cathodic current flowing through each of electrodes E10 and E11 is incrementally decreased from 50% to 0%. As a result, the electrical stimulation field gradually moves from the position shown in FIG. 8C to the axially displaced position shown in FIG. 8A.

Figure 8G:
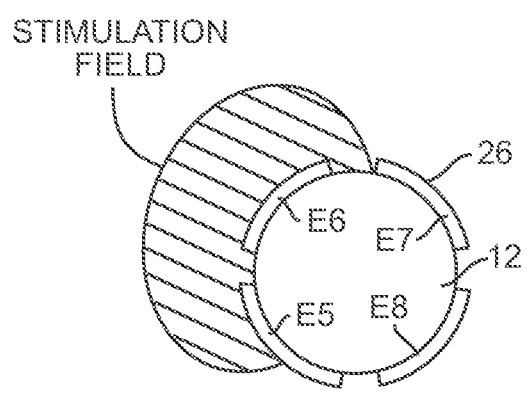

Assuming that electrodes E6 and E7 are the only electrodes in the stimulating group, the locus of the electrical stimulation field can be gradually displaced circumferentially in the counterclockwise direction about the lead 12 by gradually including electrode E5 in the stimulating electrode group and gradually excluding electrode E7 from the stimulating electrode group. That is, the fractionalized cathodic current flowing through electrode E5 is incrementally increased from 0% to 50%, while the fractionalized cathodic current flowing through electrode E7 is incrementally decreased from 50% to 0%. As a result, the electrical stimulation field gradually moves from the position shown in FIG. 8B to the circumferentially displaced position shown in FIG. 8D. One incremental step may be, e.g., where fractionalized cathodic current flowing through electrode E6 remains 50%, the fractionalized cathodic current flowing through electrode E7 is 15%, and the fractionalized cathodic current flowing through electrode E5 is 35%, in which case the electrical stimulation field may be in circumferentially displaced position, as shown in FIG. 8G.

Assuming that electrodes E5 and E6 are now the only electrodes in the stimulating group, the locus of the electrical stimulation field can be gradually displaced circumferentially in the clockwise direction about the lead 12 by gradually including electrode E7 in the stimulating electrode group and gradually excluding electrode E5 from the stimulating electrode group. That is, the fractionalized cathodic current flowing through electrode E7 is incrementally increased from 0% to 50%, while the fractionalized cathodic current flowing through electrode E5 is incrementally decreased from 50% to 0%. As a result, the electrical stimulation field gradually moves from the position shown in FIG. 8D to the circumferentially displaced position shown in FIG. 8B.

In still another method, the locus of the electrical stimulation field is electronically displaced using multiple timing channels. In particular, the electrical energy can be conveyed between different combinations of electrodes in accordance with multiple timing channels; that is, a first stimulating electrode group can be used during a first timing channel, a second stimulating electrode group can be used during a second timing channel, and so forth, and the groups may or may not overlap. The magnitude of the electrical energy conveyed in accordance with at least one of the multiple timing channels can be modified to effectively displace the locus of the stimulation region.

For example, during a first timing channel, a first stimulating group of electrodes 26 consisting of two electrodes in the second ring (electrodes E6, E7) can be activated as cathodes. During a second timing channel, a second stimulating group of electrodes 26 consisting of two electrodes in the third ring (electrodes E10, E11) can be activated as cathodes. This polarity and grouping causes electrical current to flow from the case electrode to electrodes E6 and E7 during the first timing channel in a monopolar fashion, and from the case electrode to electrodes E10 and E11 during the second timing channel in a monopolar fashion.

The first and second timing channels are simultaneously operated together, such that the electrical pulses generated at electrodes E6 and E7 are interleaved between the electrical pulses generated at electrodes E10 and E11. If the amplitude of the current of the first timing channel (controlling E6 and E7) and the amplitude of the current of the second timing channel (controlling E10 and E11) are the same, the result is effectively an overall region of stimulation region that encompasses both the stimulation field as shown in FIG. 8A and the stimulation field as shown in FIG. 8C, with an overall center position between the E6/E7 and E10/E11 contact pairs.

It can be appreciated from this that the magnitude of the electrical energy at electrodes E6 and E7 during the first timing channel and/or the electrical energy at electrodes E10 and E11 during the second timing channel can be modified to gradually displace the locus of the electrical stimulation field along the lead 12. For example, if the pulse amplitude and/or pulse duration of the electrical energy at electrodes E10 and E11 during the second timing channel is increased relative to the pulse amplitude and/or pulse duration of the electrical energy at electrodes E6 and E7 during the first timing channel, the locus of the electrical stimulation field will be effectively displaced axially in the distal direction closer to the position equidistant between electrodes E10) and E11. In contrast, if the pulse amplitude and/or pulse duration of the electrical energy at electrodes E10 and E11 during the second timing channel is decreased relative to the pulse amplitude and/or pulse duration of the electrical energy at electrodes E6 and E7 during the first timing channel, the locus of the electrical stimulation field will be effectively displaced axially in the proximal direction closer to the position equidistant between electrodes E6 and E7. It is appreciated that if there is neural tissue that is affected by both timing channels, the stimulation rate will be some composite of the effects of the two timing channels in that tissue region.

As still another example, during a first timing channel, a first stimulating group of electrodes 26 consisting an electrode in the second column (electrode E6) and an electrode in the third column (electrode E7) can be activated as cathodes. During a second timing channel, a second stimulating group of electrodes 26 consisting an electrode in the first column (electrode E5) and an electrode in the second column (electrode E6) can be activated as cathodes. This polarity and grouping causes electrical current to flow from the case electrode to electrodes E6 and E7 during the first timing channel in a monopolar fashion, and from the case electrode to electrodes E5 and E6 during the second timing channel in a monopolar fashion.

The first and second timing channels are simultaneously operated together, such that the electrical pulses generated at electrodes E6 and E7 are interleaved between the electrical pulses generated at electrodes E5 and E6. If the amplitude of the current of the first timing channel (controlling E6 and E7) and the amplitude of the current of the second timing channel (controlling E5 and E6) are the same, the result is effectively an overall region of stimulation region that encompasses both the stimulation field as shown in FIG. 8B and the stimulation field as shown in FIG. 8D, with an overall center position between the E6/E7 and E5/E6 contact pairs.

It can be appreciated from this that the magnitude of the electrical energy at electrodes E6 and E7 during the first timing channel and/or the electrical energy at electrodes E5 and E6 during the second timing channel can be modified to gradually circumferentially displace the locus of the electrical stimulation field about the lead 12. For example, if the pulse amplitude and/or pulse duration of the electrical energy at electrodes E5 and E6 during the second timing channel is increased relative to the pulse amplitude and/or pulse duration of the electrical energy at electrodes E6 and E7 during the first timing channel, the locus of the electrical stimulation field will be effectively displaced circumferentially in the counterclockwise direction closer to the position equidistant between electrodes E5 and E6. If the pulse amplitude and/or pulse duration of the electrical energy at electrodes E5 and E6 during the second timing channel is decreased relative to the pulse amplitude and/or pulse duration of the electrical energy at electrodes E6 and E7 during the first timing channel, the locus of the electrical stimulation field will be effectively displaced circumferentially in the clockwise direction closer to the position equidistant between electrodes E6 and E7. It should also be noted that timing channels can stimulate multiple loci that are not spatially contiguous, and the changing the relative amplitudes can change the amount of stimulated tissue at each of the multiple loci.

The electrical stimulation field may be modified in manners other than displacing its locus from one location to another location within the electrode array 12. For example, the electrical stimulation field may be modified by expanding or contacting the electrical stimulation field about its locus.

In one method, different electrodes can be discretely selected in the same manner discussed above with respect to the displacement of the locus of the electrical stimulation field, with the exception that the size of the electrical stimulation field is expanded or contracted.

Figure 9A:
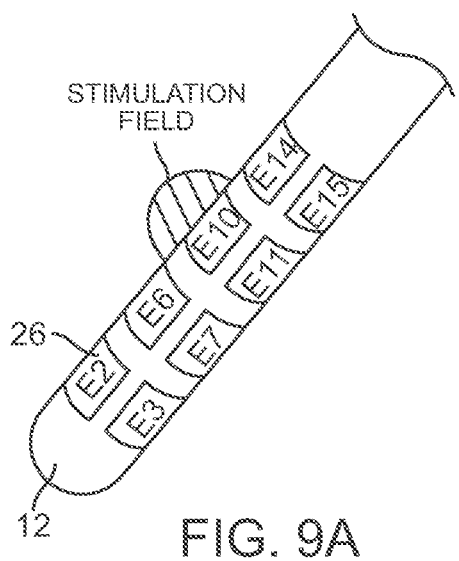
FIGS. 9A-9D are views showing activation of the electrodes to axially and circumferentially expand/contract the electrical stimulation field.
Figure 9B:
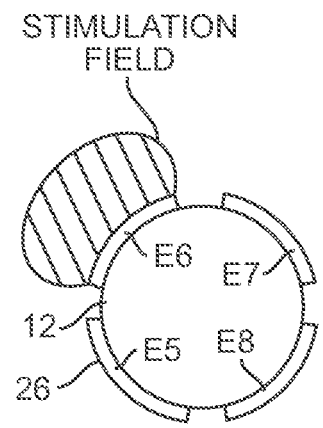

For example, as shown in FIG. 9A and 9B, a first stimulating group of electrodes 26 consisting of an electrode in the second ring and the second column (electrode E6) can be activated as a cathode. This polarity and grouping causes electrical current to flow from the case electrode to electrode E6 in a monopolar fashion, which results in an electrical stimulation field adjacent this electrode.

Figure 9C:
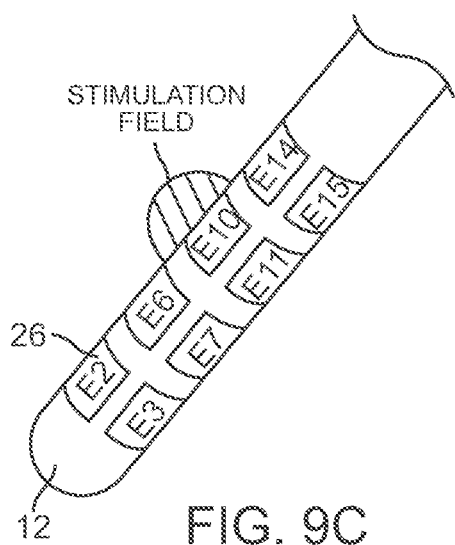

As shown in FIG. 9C, a second stimulating group of electrodes 26 consisting of three electrodes in the second column (electrodes E2, E6, E10) can be activated as cathodes. This polarity and grouping causes electrical current to flow from the case electrode to electrodes E2, E6, and E10 in a monopolar fashion, which results in an electrical stimulation field that spans these three electrodes. Thus, it can be appreciated from this that the electrical stimulation field can be axially expanded along the lead 12 by switching from the first stimulating group of electrodes (electrodes E6) to the second stimulating group of electrodes (electrodes E2, E6, E10). In contrast, the electrical stimulation field can be axially contracted along the lead 12 by switching from the second stimulating group of electrodes (electrode E2, E6, E10) to the first group of stimulating electrodes (electrode E6).

Figure 9D:
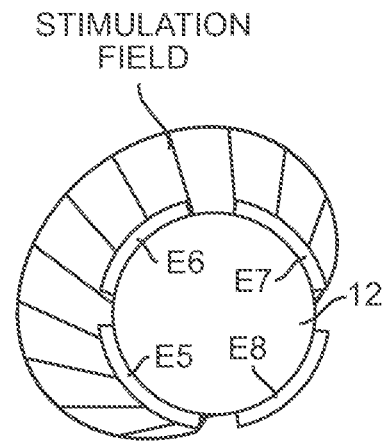

As shown in FIG. 9D, a third stimulating group of electrodes 26 consisting of three electrodes in the second ring (electrodes E5, E6, E7) can be activated as cathodes. This polarity and grouping causes electrical current to flow from the case electrode to electrodes E5, E6, and E7 in a monopolar fashion, which results in an electrical stimulation field that spans these three electrodes. Thus, it can be appreciated from this that the electrical stimulation field can be circumferentially expanded about the lead 12 by switching from the first stimulating group of electrodes (electrode E6) to the third stimulating group of electrodes (electrodes E5, E6, E7). In contrast, the electrical stimulation field can be circumferentially contracted about the lead 12 by switching from the second stimulating group of electrodes (electrodes E5, E6, E7) to the first stimulating group of electrodes (E6).

Although the electrical stimulation field has been described as above as being expanded or contracted equally around its locus, it should be noted that the electrical stimulation field may be expanded or contracted asymmetrically about the initial locus. For example, an electrical stimulation field may be axially expanded or contracted in distal direction without being expanded or contracted in the proximal direction, or the electrical stimulation field can be circumferentially expanded or contracted in the counterclockwise direction without being expanded or contracted in the clockwise direction In another method, electrical current can be gradually "steered" or shifted between electrodes to expand and contract the electrical stimulation field in a similar manner described above with respect to the displacement of the locus of the electrical stimulation field, with the exception that the locus of the electrical stimulation field is maintained, and instead the electrical stimulation field is expanded or contracted.

For example, assuming that electrode E6 is the only electrode in the stimulating group, the electrical stimulation field can be gradually expanded axially along the lead 12 by gradually including electrodes E2 and E10 in the stimulating electrode group. That is, the fractionalized cathodic current flowing through each of electrodes E2 and E10 is incrementally increased from 0% to 33 ⅓%, while the fractionalized cathodic current flowing through electrode E6 is incrementally decreased from 100% to 33 ⅓%. As a result, the electrical stimulation field gradually expands from its footprint, as shown in FIG. 9A, to an axially expanded footprint, as shown in FIG. 9C. Assuming that electrodes E2, E6, and E10 are now the only electrodes in the stimulating group, the electrical stimulation field can be gradually contracted axially along the lead 12 by gradually excluding electrodes E2 and E10 from the stimulating electrode group. That is, the fractionalized cathodic current flowing through each of electrodes E2 and E10 is incrementally decreased from 33 ⅓% to 0%, while the fractionalized cathodic current flowing through electrode E6 is incrementally increased from 33 ⅓% to 100%. As a result, the electrical stimulation field gradually contracts from its footprint, as shown in FIG. 9C, to an axially contracted footprint, as shown in FIG. 9A.

As another example, assuming that electrode E6 is the only electrode in the stimulating group, the electrical stimulation field can be gradually expanded circumferentially about the lead 12 by gradually including electrodes E5 and E7 in the stimulating electrode group. That is, the fractionalized cathodic current flowing through each of electrodes E5 and E7 is incrementally increased from 0% to 33 ⅓%, while the fractionalized cathodic current flowing through electrode E6 is incrementally decreased from 100% to 33

⅓%. As a result, the electrical stimulation field gradually expands from its footprint, as shown in FIG. 9B, to an axially expanded footprint, as shown in FIG. 9D. Assuming that electrodes E5, E6, and E7 are now the only electrodes in the stimulating group, the electrical stimulation field can be gradually contracted circumferentially about the lead 12 by gradually excluding electrodes E5 and E7 from the stimulating electrode group. That is, the fractionalized cathodic current flowing through each of electrodes E5 and E7 is incrementally decreased from 33 ⅓% to 0%, while the fractionalized cathodic current flowing through electrode E6 is incrementally increased from 33 ⅓% to 100%. As a result, the electrical stimulation field gradually contracts from its footprint, as shown in FIG. 9D, to an axially contracted footprint, as shown in FIG. 9B.

In still another method, the electrical stimulation field can be gradually expanded or contracted using multiple timing channels.

For example, during a first timing channel, a first stimulating group of electrodes 26 consisting of an electrode in the second ring (electrode E6) can be activated as a cathode. During a second timing channel, a second stimulating group of electrodes 26 consisting of three electrodes respectively in the first, second and third rings (electrodes E2, E6, E10) can be activated as cathodes. This polarity and grouping causes electrical current to flow from the case electrode to electrodes E6 during the first timing channel in a monopolar fashion, and from the case electrode to electrodes E2, E6, and E10 during the second timing channel in a monopolar fashion.

The first and second timing channels are simultaneously operated together, such that the electrical pulses generated at electrode E6 are interleaved between the electrical pulses generated at electrodes E2, E6, and E10, effectively resulting in a single electrical stimulation field that covers an area that spans only electrode E6 to an area that spans electrodes E2, E6, and E10, although in any given instant of time, the electrical stimulation field will either span only electrode E6, as shown in FIG. 9A, or span electrodes E2, E6, and E10, as shown in FIG. 9C.

It can be appreciated from this that the magnitude of the electrical energy at electrodes E6 during the first timing channel and/or the electrical energy at electrodes E2, E6, and E10 during the second timing channel can be modified to gradually expand or contract the electrical stimulation field axially along the lead 12. For example, if the pulse amplitude and/or pulse duration of the electrical energy at electrodes E2, E6, and E10 during the second timing channel is increased relative to the pulse amplitude and/or pulse duration of the electrical energy at electrode E6 during the first timing channel, the electrical stimulation field will be effectively axially expanded along the lead 12. In contrast, if the pulse amplitude and/or pulse duration of the electrical energy at electrodes E2, E6, and E10 during the second timing channel is decreased relative to the pulse amplitude and/or pulse duration of the electrical energy at electrode E6 during the first timing channel, the electrical stimulation field will be effectively axially contracted along the lead 12.

As another example, during a first timing channel, a first stimulating group of electrodes 26 consisting of an electrode in the second column (electrode E6) can be activated as a cathode. During a second timing channel, a second stimulating group of electrodes 26 consisting of three electrodes respectively in the first, second, and third columns (electrodes E5, E6, E7) can be activated as cathodes. This polarity and grouping causes electrical current to flow from the case electrode to electrodes E6 during the first timing channel in a monopolar fashion, and from the case electrode to electrodes E5, E6, and E7 during the second timing channel in a monopolar fashion.

The first and second timing channels are simultaneously operated together, such that the electrical pulses generated at electrode E6 are interleaved between the electrical pulses generated at electrodes E5, E6, and E7 effectively resulting in a single electrical stimulation field that covers an area that spans only electrode E6 to an area that spans electrodes E5, E6, and E7, although in any given instant of time, the electrical stimulation field will either span only electrode E6, as shown in FIG. 9B, or span electrodes E5, E6, and E7, as shown in FIG. 9D.

It can be appreciated from this that the magnitude of the electrical energy at electrodes E6 during the first timing channel and/or the electrical energy at electrodes E2, E6, and E10 during the second timing channel can be modified to gradually expand or contract the electrical stimulation field circumferentially about the lead 12. For example, if the pulse amplitude and/or pulse duration of the electrical energy at electrodes E5, E6, and E7 during the second timing channel is increased relative to the pulse amplitude and/or pulse duration of the electrical energy at electrode E6 during the first timing channel, the electrical stimulation field will be effectively circumferentially expanded about the lead 12. In contrast, if the pulse amplitude and/or pulse duration of the electrical energy at electrodes E5, E6, and E7 during the second timing channel is decreased relative to the pulse amplitude and/or pulse duration of the electrical energy at electrode E6 during the first timing channel, the electrical stimulation field will be effectively circumferentially contracted about the lead 12.

It should be noted that although the modification of the electrical stimulation field has been described with respect to a single lead, the electrical stimulation field can be modified relative to multiple leads by assuming ideal poles and computationally determining the stimulation parameters necessary to emulate the ideal poles, as described in U.S. Provisional Application Ser. No. 61/257,753, entitled "System and Method for Mapping Arbitrary Electric Fields to Pre-existing Lead Electrodes," which is incorporated herein by reference.

Figure 10:
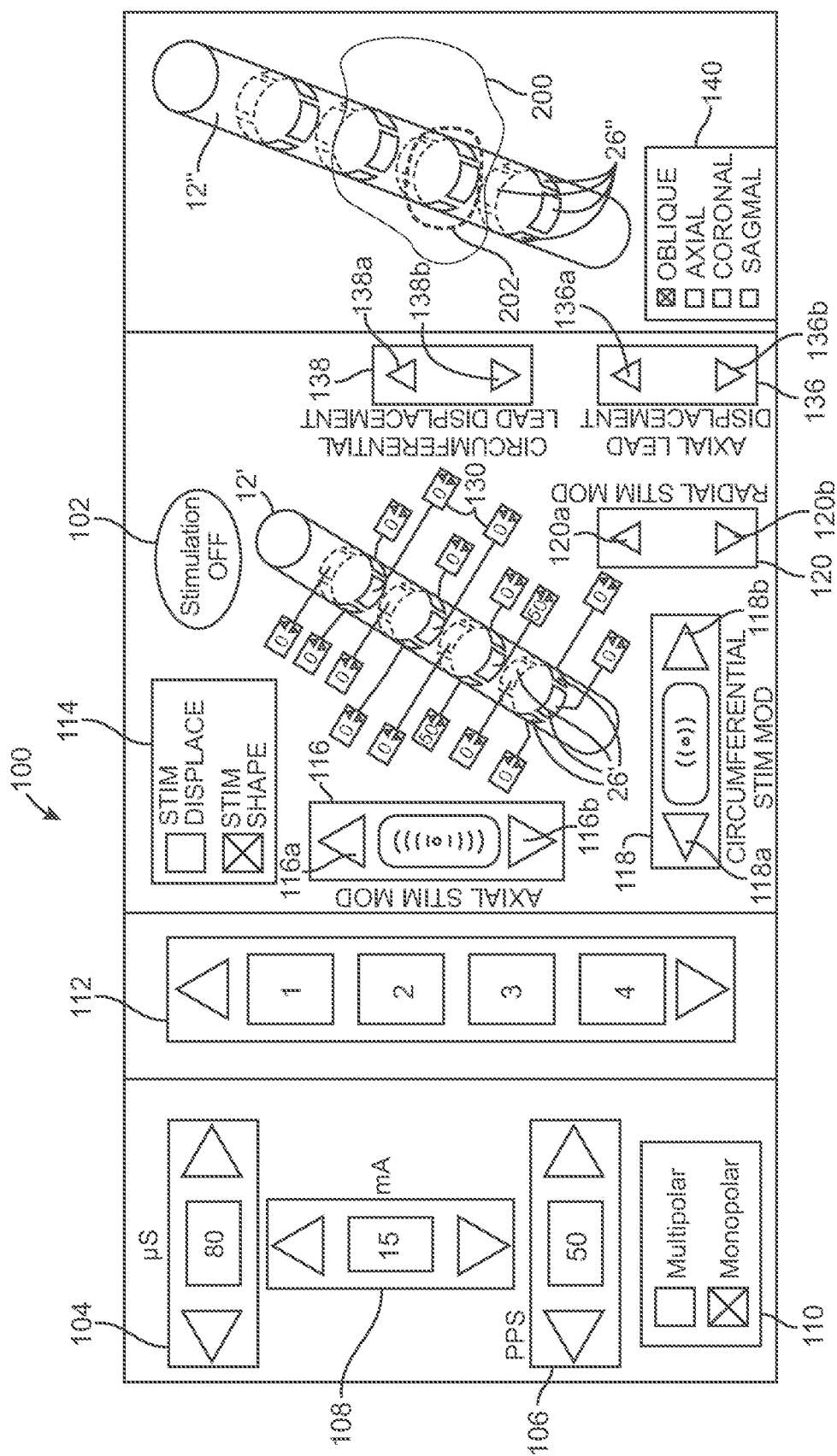
FIG. 10 is a plan view of a user interface of the CP of FIG. 7 for programming the IPG of FIG. 2.

Returning now to the operation of the user interface of the CP 16, a programming screen 100 can be generated by the CP 16, as shown in FIG. 10. The programming screen 100 allows a user to perform stimulation parameter testing.

The programming screen 100 further comprises a stimulation on/off control 102 that can be alternately clicked to turn the stimulation on or off. The programming screen 100 further includes various stimulation parameter controls that can be operated by the user to manually adjust stimulation parameters. In particular, the programming screen 100 includes a pulse width adjustment control 104 (expressed in microseconds (µs)), a pulse rate adjustment control 106 (expressed in pulses per second (pps)), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 40 of the IPG 14 may be treated as one of the lead electrodes 26, such that both the case electrode 40 and at least one of the lead electrodes 26 can be used to convey anodic electrical current at the same time.

The programming screen 100 also includes an electrode combination control 112 having arrows that can be clicked by the user to select one of three different electrode combinations 1-4. Each of the electrode combinations 1-4 can be created using a variety of control elements.

The user interface includes a mode selection control element 114 and two sets of electrical stimulation field modification control elements—a set of axial modification control elements 116 and a set of circumferential modification control elements 118. In the illustrated embodiments, the mode selection control element 114 and sets of field modification control elements 116, 118, as well as the other control elements discussed herein, are implemented as a graphical icon that can be clicked with a mouse or touched with a finger in the case of a touchscreen. Alternatively, the control elements described herein may be implemented as mechanical buttons, keys, sliders, etc. that can be pressed or otherwise moved to actuate the control elements.

When the mode selection control element 114 is actuated, the processor 80 is configured for selectively placing the field modification control elements in either an electrical stimulation field displacement mode, during which the processor 80 generates stimulation parameter sets designed to axially and/or circumferentially displace the locus of the electrical stimulation field relative to the axis of the lead(s) 12, as discussed above with respect to FIGS. 8A-8D, or in an electrical field stimulation field shaping mode, during which the processor 80 generates stimulation parameter sets designed to axially or circumferentially expand/contract electrical stimulation field relative to the axis of the lead(s) 12, as discussed above with respect to FIGS. 9A-9D. The output telemetry circuitry 86 is configured for transmitting these stimulation parameters sets to the IPG 14.

In the illustrated embodiment, the mode selection control element 114 includes check boxes that can be alternately clicked by the user to selectively place the field modification control elements between the electrical stimulation field displacement mode and the electrical stimulation field shaping mode. Alternatively, the mode selection control element 114 takes the form of a button that can be repeatedly clicked to toggle the field modification control elements 116, 118 between the modes.

Each of the sets of field modification control elements 116, 118 takes the form of a double arrow (i.e., two oppositely pointing control element arrows) that can be actuated to modify the electrical stimulation field depending on the mode of operation.

For example, in the field displacement mode, an upper arrow control element 116a of the set of axial modification control elements can be clicked to axially displace the locus of the electrical stimulation field (i.e., along the axis of the lead(s) 12) in the proximal direction; a lower arrow control element 116b of the set of axial modification control elements can be clicked to axially displace the locus of the electrical stimulation field (i.e., along the axis of the lead(s) 12) in the distal direction; a left arrow control element 118a of the set of circumferential control elements can be clicked to circumferentially displace the locus of the electrical stimulation field (i.e., about the axis of the lead(s) 12) in the counterclockwise direction; and a right arrow control element 118b of the set of circumferential control elements can be clicked to circumferentially displace the locus of the electrical stimulation field (i.e., about the axis of the lead(s) 12) in the clockwise direction.

In the field shaping mode, the lower arrow control element 116a of the set of axial modification control elements can be clicked to axially contract the electrical stimulation field about its locus; the upper arrow control element 116b of the set of axial modification control elements can be clicked to axially expand the electrical stimulation field about its locus; the left arrow control element 118a of the set of circumferential control elements can be clicked to circumferentially contract the electrical stimulation field about its locus; and the right arrow control element 118b of the set of circumferential control elements can be clicked to circumferentially expand the electrical stimulation field about its locus.

Thus, it can be appreciated that by virtue of the mode selection control element 114, the sets of field modification control elements 116, 118 can have a dual-function; i.e., the same control element can be operated to both displace the locus of the electrical stimulation field and shape the electrical stimulation field about its locus.

In addition, and particularly with respect to the set of circumferential modification control elements 118, the processor 80 generates stimulation parameter sets designed to circumferentially displace the locus of the electrical stimulation field about the lead(s) 12 in a first rotational direction at respective different angular positions as one of the circumferential modification control elements 118a, 118b is continually actuated; i.e., by continuously actuating one of the control elements 118a, 118b, e.g., by clicking on holding one of the control elements 118a, 118b down, or repeatedly actuating one of the control elements 118a, 118b, e.g., by repeatedly clicking and releasing one of the control elements 118a, 118b.

Thus, it can be appreciated that the left arrow control element 118a may be continually actuated, such that the locus of the electrical stimulation field is circumferentially displaced about the lead(s) 12 in a counterclockwise direction at different angular positions, and the right arrow control element 118b may be continually actuated, such that the locus of the electrical stimulation field is circumferentially displaced about the lead(s) 12 in a clockwise direction at different angular positions.

The user interface of the CP 18 optionally includes a set of radial modification control elements 120 taking the form of a double arrow (i.e., two oppositely pointing control element arrows). When the set of radial modification control elements 120 are actuated, the processor 80 is configured for generating stimulation parameter sets designed to radially displace the locus of the electrical stimulation field relative to the axis of the lead(s) 12, as discussed above with respect to FIGS. 8B and 8E. In particular, an upper arrow control element 120a of the set of radial modification control elements can be clicked to radially displace the locus of the electrical stimulation field inward towards the axis of the lead(s) 12), and a lower arrow control element 120b of the set of radial modification control elements can be clicked to radially displace the locus of the electrical stimulation field outward from the axis of the lead(s) 12). The output telemetry circuitry 86 is configured for transmitting stimulation parameters sets generated by the processor 80 to the IPG 14.

Although the indicators of the circumferential modification control elements 118a, 118b respectively take the form of left and right arrows, other indicators can be used for circumferential modification control elements dedicated to displacement of the locus of the electrical stimulation field.

For example, as shown in FIG. 11A, the control element 118c may be indicated as a counterclockwise circular arrow indicating that the locus of the electrical stimulation field will be circumferentially displaced at different angular positions in the counterclockwise direction when continually actuated, and the control element 118*d* may be indicated as a clockwise circular arrow indicating that the locus of the electrical stimulation field will be circumferentially displaced at different angular positions in the clockwise direction when continually actuated.

As shown in FIG. 11B, the control element 118*e* may be indicated as a decreasing angle indicating that the locus of the electrical stimulation field will be circumferentially displaced at different angular positions in the clockwise direction when continually actuated until the nominal angle of the electrical stimulation field is reduced to 0 degrees, and the control element 118*f* may be indicated as an increasing angle indicating that the locus of the electrical stimulation field will be circumferentially displaced at different angular positions in the counterclockwise direction when continually actuated until the nominal angle of the electrical stimulation field is increased to 360 degrees. Of note, the indicator on the control element can change when the mode selection is changed. For example, in displacement mode, indicators might be those of FIG. 11A, while in shape mode the indicators might be those of FIG. 11B.

As shown in FIG. 11C, a control element 118*g* may be indicated as an angle indicating that the locus of the electrical stimulation field will be circumferentially displaced at different angular positions in the clockwise direction when continually actuated. In this case, the angle of the electrical stimulation field wraps around, such that there is no beginning or ending of the angle.

In an optional embodiment shown in FIG. 12A, the user interface of the CP 18 optionally comprises a rotational control element 122*a* capable of being rotated about a point. The processor 80 generates a set of stimulation parameters designed to circumferentially displace a locus of the electrical stimulation field about the lead(s) 12 when the rotational control element 122*a* is rotated about the point 124, which set of stimulation parameters is then transmitted from the output circuitry 86 of the CP 18 to the IPG 14. In the illustrated embodiment, the rotational control element 122*a* is implemented as a graphical icon. In this case, the rotational control element 122*a* can simply be clicked on with a cursor (or touched) and dragged to rotate it. Alternatively, the rotational control element 122*a* can be a mechanical dial that can be physically rotated by the user.

The user interface optionally includes a marker 126 associated with the rotational control element 122*a* for indicating the circumferential position of the locus of the electrical stimulation field. In the illustrated embodiment, the marker 126 takes the form of an arrow that rotates with the rotational control element 122*a*. Alternatively, the rotational control element takes the form of an arrow 122*b*, as shown in FIG. 12B, or an arrow 122*c*, as shown in FIG. 12C, in which case, the rotational control element 122, itself, provides an indicator of the circumferential position of the locus of the electrical stimulation field. In another alternative embodiment shown in FIG. 12D, the rotational control element 122 is segmented into pie-shaped sections. In this case, the marker 126 takes the form of one or more pie-shaped sections that are highlighted when adjacent a fixed element 126 to indicate the circumferential position of the locus of the electrical stimulation field. As shown in FIG. 12E, the rotational control element 122*e* takes the form of a segmented ring, with one or more of the segments highlighted when adjacent a fixed element 126 to indicate the circumferential position of the locus of the electrical stimulation field.

Referring back to FIG. 12A, the user interface of the CP 18 optionally includes a radial modification control element 128 capable of being displaced along the radius of the rotational control element 122*a*. The processor 80 generates a set of stimulation parameters designed to radially displace the locus of the electrical stimulation field when the radial modification control element 128 is actuated, which set of stimulation parameters is then transmitted from the output circuitry 86 of the CP 18 to the IPG 14. In the illustrated embodiment, the radial modification control element 128 is implemented as a graphical icon. In this case, the radial modification control element 128 can simply be clicked on and dragged to radially displace it inward or outward. Radially inward displacement of the radial modification control element 128 displaces the locus of the electrical stimulation field radially inward towards the point about which the rotational control element 122*a* rotates, whereas radially outward displacement of the radial modification control element 128 displaces the locus of the electrical stimulation field radially outward away from the point about which the rotational control element 122*a* rotates.

Referring back to FIG. 10, programming screen 100 of the CP 18 optionally or alternatively displays a three-dimensional graphical renderings of the lead 12' and electrodes 26' and a plurality of iconic control elements 130 graphically linked to the three-dimensional electrode renderings 26'. In the illustrated embodiment, the control elements 130 are directly linked to the electrode renderings 26'. Alternatively, as shown in FIG. 13, the control elements 130 are indirectly linked to the electrode renderings 26' via reference lines 132. In either case, the processor 80 generates stimulation parameters designed to modify the electrical stimulation field when any of the these control elements 130 is actuated, which stimulation parameters are then transmitted from the output circuitry 86 of the CP 18 to the IPG 14. In the illustrated embodiment, each of the control elements 130 has an up arrow and a down arrow that can be respectively actuated (e.g., by clicking) to respectively increase or decrease the electrical current flowing through the electrode 26 corresponding to the graphical electrode rendering 26' to which the actuated control element 126 is graphically linked. The control element 126 also includes an indicator 134 that provides an indication of the amount of electrical current flowing through each of the electrodes 26 in terms of a fractionalized current value. The indicators 134 may perform this function when the respective control elements 130 are actuated or when the axial modification control elements 116, circumferential modification control elements 118, or radial modification control elements 120 are actuated.

The programming screen 100 of the CP 18 also displays other three-dimensional graphical renderings of the lead 12" and electrodes 26" relative to a graphical anatomical structure 200 that is preferably the stimulation target. For example, if the DBS indication is Parkinson's disease, the anatomical structure 200 is preferably the subthalamic nucleus (STN) or the globus pallidus (GPi). If the DBS indication is Essential Tremor, the anatomical structure 200 is preferably the thalamus. If the DBS indication is depression, the anatomical structure 200 is one or more of the nucleus acumbens, ventral striatum, ventral capsule, anterior capsule, or the Brodmann's area 25. If the DBS indication is epilepsy, the anatomical structure 200 is preferably the anterior nucleus. If the DBS indication is a gait disorder, the anatomical structure 200 is preferably the pedunculopontine (PPN). If the DBS indication is dementia, Alzheimer's disease or memory disorders, the anatomical structure 200 is preferably anywhere in the Papez circuit. The anatomical structure 200 can be obtained from any available brain atlas, or from a patient specific brain atlas derived from, e.g., a magnetic resonant imager (MRI), computed tomography (CT), X-ray, fluoroscopy, ventriculography, ultrasound, or any other imaging modality or a merging of any or all of these modalities.

Figure 14:
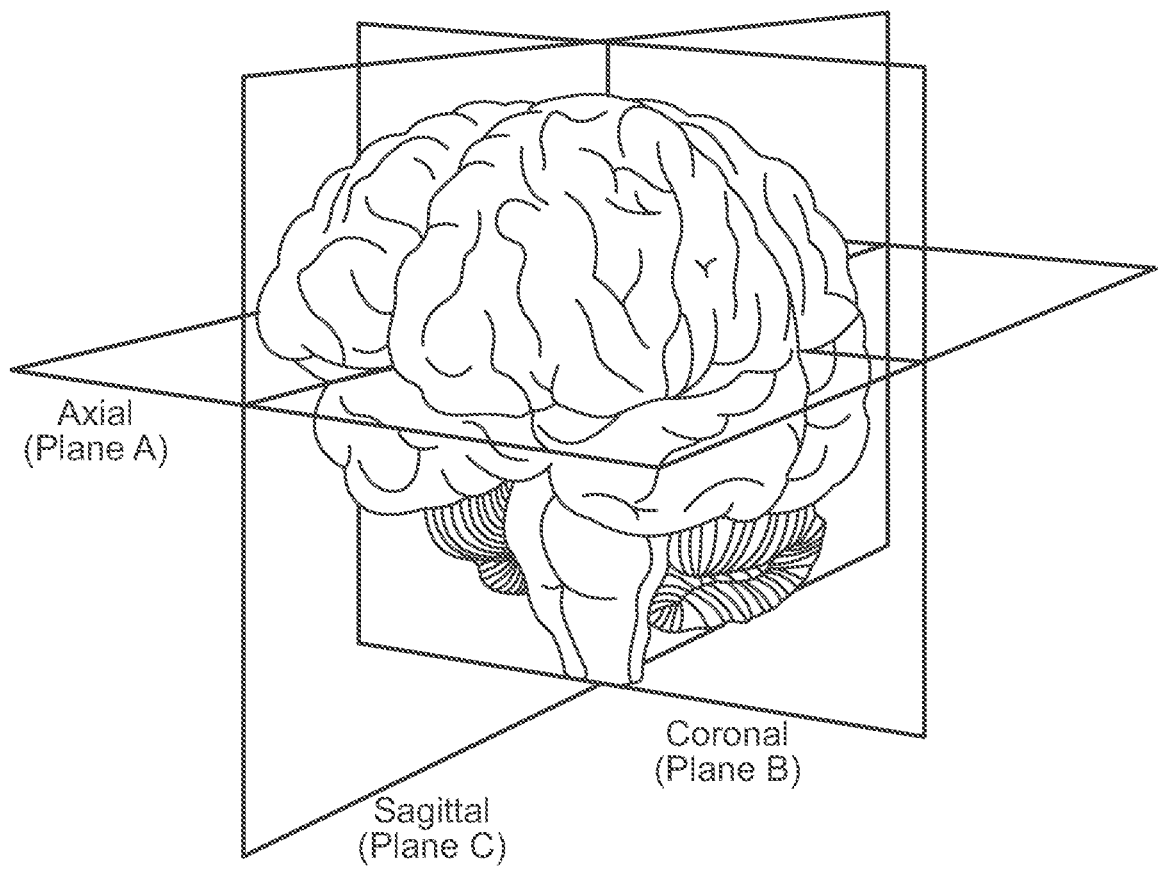
FIG. 14 is a perspective view of a brain that can be displayed in any one of a selected axial, coronal, or sagittal view generated by the user interface of FIG. 10 to analyze a volume of activation.

Based on the current stimulation parameter set, the processor 80 estimates a resulting volume of tissue activation (VTA) 202, and displays it with the graphical lead 12" and graphical anatomical structure 200. In the preferred embodiment, the VTA 202 is superimposed over the graphical anatomical structure 200. In the illustrated embodiment, although the graphical lead 12", graphical anatomical structure 200, and VTA 202 are displayed in an oblique view, they can be alternatively displayed in any one or more of traditional planes of section (e.g., axial, coronal, and sagittal), as shown in FIG. 14. The user can specify the general shape of the VTA 202 (e.g., spherical, ovoid, etc.) in any coordinate space desired, e.g., Tailerach, Horsely-Clark, Cartesian, etc. Or the margins of the VTA 202 can be clicked on and dragged to the user's specifications. In an optional embodiment, the user may thumb through the images in each plane simultaneously or though one plane of section at a time by selecting one of the check boxes in a view control element 140.

In one embodiment, the user can remove different sections (octants) of the brain, for example, the one closest to the viewer in FIG. 14 and demarcated (outlined) by planes A (axial), B (coronal) and C (sagittal). The user can remove any one or several of these 8 "blocks" of tissue to visualize the target tissue or VTA 202. The user can then visualize the target or VTA 202 projected onto any one, two or all three of the planes of section. The user can move the planes independently to scroll through sections in each plane. For example, the user could move plane A up and down independent of the other sections to view the target or VTA 202 projection onto different adjacent sections. Similarly, the user could move planes B or C independent of the other two planes to visualize the target or VTA 202 in adjacent sections. The user can also rotate the entire 3-D structure to view the target or VTA 202 from any angle.

The programming screen 100 further includes a set of axial lead displacement control elements 138 and a set of circumferential lead displacement control elements 138 that can be actuated to synchronously displace both the graphical lead 12' with the control elements 130 and the graphical lead 12" and associated VTA 202 relative to the graphical anatomical structure 200.

When the set of axial lead displacement control elements 136 are actuated, the processor 80 is configured for synchronously and axially displacing both the graphical lead 12' and the graphical lead 12" and associated VTA 202 in the same direction by the same distance (i.e., moving the graphical leads 12', 12" and VTA 202 along the respective axes of the graphical leads the same linear distance). In particular, an upper arrow control element 136a of the set of axial lead displacement control elements can be clicked to axially displace the graphical lead 12' and the graphical lead 12" and associated VTA 202 relative to the anatomical structure 200 in the proximal direction, and a lower arrow control element 136b of the set of axial lead displacement control elements can be clicked to axially displace the graphical lead 12' and the graphical lead 12" and associated VTA 202 relative to the anatomical structure 200 in the distal direction.

When the set of circumferential lead displacement control elements 138 are actuated, the processor 80 is configured for synchronously and circumferentially displacing both the graphical lead 12' and the graphical lead 12" and associated VTA 202 in the same direction by the same distance (i.e., rotating the graphical leads 12', 12" and VTA 202 about the respective axes of the graphical leads the same angular distance). In particular, an upper arrow control element 138a of the set of circumferential lead displacement control elements can be clicked to circumferentially displace the graphical lead 12' and the graphical lead 12" and associated VTA 202 relative to the anatomical structure 200 in the counterclockwise direction, and a lower arrow control element 138b of the set of circumferential lead displacement control elements can be clicked to circumferentially displace the graphical lead 12' and the graphical lead 12" and associated VTA 202 relative to the anatomical structure 200 in the clockwise direction.

Although the foregoing techniques have been described as being implemented in the CP 16, it should be noted that this technique may be alternatively or additionally implemented in the RC 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for use with a neurostimulation system having one or more neurostimulation leads carrying a plurality of electrodes capable of conveying an electrical stimulation field into tissue in which the electrodes are implanted, comprising:

a user interface including a representation of the electrodes and a rotational control element configured for being actuated by rotating the rotational control element about a point;

a processor configured for generating a set of stimulation parameters to rotationally displace a locus of the electrical stimulation field as indicated by the rotational control element by controlling a selection of one or more electrodes from the plurality of electrodes and controlling an adjustable fractionalization of a total amount of current flowing collectively through the selected one or more electrodes when the rotational control element is actuated, wherein the fractionalization describes, for each of the selected one or more electrodes, what fraction of the total amount of current flows through that electrode; and output circuitry configured for transmitting the set of stimulation parameters to the neurostimulation system.

2. The external control device of claim 1, wherein the user interface further includes a representation of an estimate of a volume of tissue activation generated using the set of stimulation parameters and the electrodes and a first circumferential modification control element and a second circumferential modification control element configured for being actuated;

wherein the processor is further configured for generating stimulation parameters designed to circumferentially contract the representation of the estimate of the volume of tissue activation in response to actuation of the first circumferential modification control element and for generating stimulation parameters designed to circumferentially expand the representation of the estimate of the volume of tissue activation in response to actuation of the second circumferential modification control element.

3. The external control device of claim 2, wherein the user interface further comprises a representation of a portion of at least one of the one or more neurostimulation leads.

4. The external control device of claim 2, the user interface further comprises a circumferential stimulation displacement control element configured for being actuated, the processor is further configured for generating stimulation parameters designed to circumferentially displace the representation of the estimate of the volume of tissue activation about the one or more neurostimulation leads in a rotational direction in response to actuation of the circumferential stimulation displacement control element.

5. The external control device of claim 2, wherein the user interface further comprises a radial modification control element, the processor is further configured for generating stimulation parameters designed to radially displace the representation of the estimate of the volume of tissue activation in response to actuation of the radial modification control element.

6. The external control device of claim 2, wherein the user interface further comprises an axial modification control element, the processor is further configured for generating stimulation parameters designed to axially displace the representation of the estimate of the volume of tissue activation in response to actuation of the axial modification control element.

7. The external control device of claim 2, wherein the user interface further comprises an axial modification control element, the processor is further configured for generating stimulation parameters designed to axially expand or contract the representation of the estimate of the volume of tissue activation in response to actuation of the axial modification control element.

8. The external control device of claim 2 wherein the user interface further includes a representation of an anatomical structure and the representation of the anatomical structure is divided into segments and the processor is configured for removing, in response to user input, one or more of the segments of the anatomical structure to visualize a target or the estimate of the volume of tissue activation.

9. The external control device of claim 8, wherein the anatomical structure is a brain and the brain is demarcated by axial, coronal, and sagittal planes.

10. The external control device of claim 9, wherein the processor is configured for moving, in response to user input, one or more of the axial, coronal, or sagittal planes.

11. The external control device of claim 2, wherein the user interface further comprises a representation of an anatomical structure, an axial lead displacement control element, and a circumferential lead displacement control element, the processor is further configured for generating stimulation parameters designed to axially displace the representation of the electrodes and the representation of the estimate of the volume of tissue activation relative to the representation of the anatomical structure in response to actuation of the axial lead displacement control element and to circumferentially displace the representation of the electrodes and the representation of the estimate of the volume of tissue activation relative to the representation of the anatomical structure in response to actuation of the circumferential lead displacement control element.

12. The external control device of claim 1, wherein the rotational control element is a mechanical dial that can be physically rotated by a user.

13. The external control device of claim 1, wherein the rotational control element takes a form of an icon that can be dragged to rotate it.

14. The external control device of claim 1, wherein the user interface further comprises a marker associated with the rotational control element for indicating a circumferential position of the locus of the electrical stimulation field.

15. The external control device of claim 14, wherein the marker takes a form of a rotatable arrow.

16. The external control device of claim 14, wherein the marker takes a form of a rotatable arrowhead.

17. The external control device of claim 1, wherein the rotational control element is segmented into pie-shaped sections Which are selected when adjacent an element that indicates a circumferential position of the locus of the electrical stimulation field.

18. The external control device of claim 17, wherein the user interface further comprises a marker associated with the rotational control element for indicating a circumferential position of the locus of the electrical stimulation field, wherein the marker takes a form of one or more of the pie-shaped sections being highlighted.

19. The external control device of claim 1, wherein the rotational control element takes a form of a ring of segments which are selected when adjacent an element that indicates a circumferential position of the locus of the electrical stimulation field.

20. The external control device of claim 19, wherein the user interface further comprises a marker associated with the rotational control element for indicating a circumferential position of the locus of the electrical stimulation field, wherein the marker takes a form of one or more of the segments being highlighted.

* * * * *